(12) United States Patent (10) Patent No.: US 8,931,487 B2
Razmovski (45) Date of Patent: Jan. 13, 2015

(54) ORAL CAVITY MANIPULATOR

(76) Inventor: John Razmovski, Seddon (AU)

( * ) Notice: Subject to any disclaimer, the term of this patent is extended or adjusted under 35 U.S.C. 154(b) by 1162 days.

(21) Appl. No.: 12/664,391

(22) PCT Filed: Jun. 16, 2008

(86) PCT No.: PCT/AU2008/000846
§ 371 (c)(1),
(2), (4) Date: Dec. 14, 2009

(87) PCT Pub. No.: WO2008/151374
PCT Pub. Date: Dec. 18, 2008

(65) Prior Publication Data
US 2010/0132720 A1 Jun. 3, 2010

(30) Foreign Application Priority Data
Jun. 15, 2007 (AU) ................................. 2007202799

(51) Int. Cl.
*A61F 5/56* (2006.01)
(52) U.S. Cl.
CPC ..................................... *A61F 5/566* (2013.01)
USPC ........................................................... 128/848
(58) Field of Classification Search
CPC .................................... A61F 5/56; A61F 5/566
USPC ......... 128/848, 846, 861; 602/902; 433/6, 19, 433/140
See application file for complete search history.

(56) References Cited

U.S. PATENT DOCUMENTS

| | | | |
|---|---|---|---|
| 3,132,647 A * | 5/1964 | Giuseppe | 128/848 |
| 4,169,473 A | 10/1979 | Samelson | |
| 4,304,227 A | 12/1981 | Samelson | |
| 5,117,816 A | 6/1992 | Shapiro | |
| 5,154,184 A | 10/1992 | Alvarez | |
| 6,129,084 A | 10/2000 | Bergersen | |

(Continued)

FOREIGN PATENT DOCUMENTS

| | | |
|---|---|---|
| AU | 1995038013 A1 | 8/1996 |
| AU | 2000012303 | 7/2001 |

(Continued)

OTHER PUBLICATIONS

International Preliminary Report on Patentability completed Mar. 18, 2009, in International Application No. PCT/AU2008/000846, filed Jun. 16, 2008, 4 pages.

(Continued)

*Primary Examiner* — Victoria J Hicks
(74) *Attorney, Agent, or Firm* — Christensen O'Connor Johnson Kindness PLLC

(57) ABSTRACT

An oral cavity manipulator for controlling the position of tongue and jaw, the manipulator including a foundation body, maxilla and mandibular teeth engaging elements mountable on the foundation body and having width equal to or greater than the width of the foundation body and including teeth receiving portions for in use receiving the teeth of the user, a tongue position means attached to one of the foundation body, or the teeth engaging elements wherein in an operating condition the mandibular teeth engaging element is selectively located on the foundation body forward of the maxilla teeth engaging element to receive and locate the mandible of a user forward of the maxilla and position the tongue between the teeth elements to substantially maintain unobstructed airways at the throat of the user.

9 Claims, 13 Drawing Sheets

(56) References Cited

U.S. PATENT DOCUMENTS

| | | |
|---|---|---|
| 6,408,852 B2 | 6/2002 | Tielemans |
| 6,467,484 B1 | 10/2002 | De Voss |
| 2001/0027793 A1 | 10/2001 | Tielemans |
| 2005/0028827 A1 | 2/2005 | Halstrom |
| 2005/0150504 A1* | 7/2005 | Heeke et al. .................. 128/848 |
| 2010/0288288 A1* | 11/2010 | Hegde et al. .................. 128/848 |

FOREIGN PATENT DOCUMENTS

| | | |
|---|---|---|
| CA | 2 206 701 A1 | 6/1996 |
| CA | 2 277 504 A1 | 1/2001 |
| DE | 3442669 | 5/1986 |
| DE | 3442670 | 5/1986 |
| DE | 195 03 288 C1 | 7/1996 |
| DE | 298 22 336 U1 | 5/1999 |
| DE | 299 05 809 U1 | 7/1999 |
| DE | 100 11 687 A1 | 11/2000 |
| EP | 0 182 387 A1 | 5/1986 |
| EP | 0 801 937 A1 | 10/1997 |
| JP | 2000/232987 | 8/2000 |
| WO | 96/16618 A1 | 6/1996 |
| WO | WO-96/16618 | 6/1996 |
| WO | 01/30260 A1 | 5/2001 |
| WO | 2006/063403 A1 | 6/2006 |

OTHER PUBLICATIONS

Australian Patent Examination Report No. 1 issued Nov. 8, 2012, in Australian Patent Application No. 2008261614, filed Jun. 16, 2008, 2 pages.

Supplementary Partial European Search Report completed Jan. 4, 2011, in European Application No. 08 75 6927, filed Mar. 10, 2010, 3 pages.

* cited by examiner

ORAL CAVITY MANIPULATOR

FIELD OF THE INVENTION

The present invention relates to an oral cavity manipulator for use to substantially prevent obstruction of a user's airways. In particular the present invention relates to an oral cavity manipulator for substantially minimising snoring and Obstructive Sleep Apnoea (OSA).

BACKGROUND OF THE INVENTION

Obstructive Sleep Apnoea (OSA) is a disease, which affects many people. Symptoms of the disease OSA manifest themselves in the form of fatigue, tiredness, poor concentration, mood changes and in some instances impotence has been reported. If left untreated or undiagnosed the disease can be very debilitating and even fatal. It is known that sufferer's of OSA are more likely to have motor vehicle accidents and are at greater risk of heart attack and stroke.

A characteristic of OSA is the substantial gasping for air during a waking period. This results from the presence of an occluded airway requiring a need to expend a substantial inspiratory effort to overcome occlusion and to initiate the waking phase. Occlusion or blockage of airways can be caused by muscle relaxation of the throat during sleep or a sufferer's tongue. Risk factors associated with OSA include weight gain, alcohol consumption, sleeping position and intake of sedatives. It has been postulated that excess weight in the neck reduces the ability of the pharyngeal muscles to maintain a lumen (opening) during sleep. In this case weight loss may be sufficient to address sleep problems associated with OSA.

A number of treatment regimens have been provided for OSA sufferers. For example people exhibiting an increased episodic severity may require positive pressure therapy (PPT) or wearing of an oral appliance. The most common form of PPT is referred to as 'continuous positive airway pressure' (CPAP). In general CPAP is administered through a nasal or face-mask strapped to a person's head. The face-mask is connected to an air compressor via a hose and the compressor sends air under pressure through the hose into the mask. The positive air pressure blows open the pharynx and prevents the airway from collapsing. Such a device however suffers from the disadvantage(s) that it is not aesthetically pleasing; is relatively expensive; is uncomfortable; can initiate nose bleeds and renders the nose and sinus cavity feeling dry.

Oral appliances have been used for the treatment of OSA including mandibular advancement devices, which involve pulling the mandible (lower jaw) forward relative to the maxilla (upper jaw). Mandibular advancement devices are generally less expensive than CPAP devices and therefore offer an economic alternative. The problem with such devices however is that the tongue may still interfere with the airway opening particularly when a sufferer moves the position of his/her head. In many instances rolling of the tongue may result in airway obstruction thus lowering the efficiency of an oral mandibular advance device. Hence further improvements in oral appliances are required to help reduce episodes of OSA.

It should be noted that any discussion of prior art does not constitute an admission of the state of the common general knowledge.

One object of the invention is therefore to provide an alternative oral cavity appliance that substantially addresses one or more of the problems of the prior art.

SUMMARY OF THE INVENTION

The present invention provides an oral cavity manipulator including:
a foundation body having a mounting portion and a tongue depression portion adjacent the mounting portion, the body providing at least one airflow pathway therethrough;
maxilla and mandibular teeth engaging elements including teeth receiving portions, wherein the teeth engaging elements are adapted to be adjustably received on the mounting portion of the body so that the maxilla and mandibular elements can be selectively positioned relative to each other,
wherein in an operating condition the mandibular teeth engaging element is slidably positioned on the mounting portion of the body forward of the maxilla element to locate the mandible forward of the maxilla and wherein the tongue depression means urges against a surface portion of a user's tongue, close to the throat to substantially maintain unobstructed airways.

The oral cavity manipulator can include a tongue receiving structure. The tongue receiving structure can be mounted to a forward portion of the maxilla teeth engaging element. The oral cavity manipulator can include oppositely disposed flange elements adjacent the tongue depression means to laterally urge curtain portions of the throat of a user.

The maxilla and mandibular teeth engaging elements can include a base plate mounted to respective teeth receiving portions. The each base plate includes oppositely disposed mounting flange members wherein the flange members can be slidably received on the mounting portion of the body. The maxilla and mandibular teeth engaging elements can be mounted to the mounting portions of the body such that the teeth engaging elements can be altered to suit the shape of a user's oral cavity.

The tongue depression portion can be adjustable. In this of the present invention, the oral cavity manipulator is adjustable to alter the angle of the tongue depression element relative to the maxilla and mandibular appliances. A user can therefore make adjustments to suit the force required to displace the tongue away from an airway obstructing position.

In addition the tongue depression portion can include a removable sheath. The tongue depression portion of the foundation body can be adjusted relative to the plane of the mounting portion of the body to urge against a base surface portion of the user's tongue, close to the throat. The tongue depression portion can therefore extend beneath the plane of the mounting portion. The positioning of the tongue depression portion relative to the mounting portion of the body allows the depression portion to positively urge against a base surface portion of the user's tongue, close to the throat, when the oral cavity appliance is operatively fitted/positioned. The depression means can be substantially u- or v-shaped.

When the oral cavity manipulator is in a fitted condition, the user's tongue is urged forward of and away from the epiglottis or obstructive position, hence lessens the ability of the tongue to create an airway obstruction. The user's tongue is thus able to be urged forward as well as down away from an obstructive position.

The maxilla and mandibular teeth receiving portions include a generally u-shaped structure having a floor and dependent wall forming a cross-sectional u-shaped recess for receiving teeth therein. The u-shaped recess can include an impression composition for creating an impression fitting for a user's upper and lower dental arch.

In a related aspect of the invention there is provided an oral cavity manipulator for use in substantially preventing incidences of OSA or snoring, the manipulator including:

a foundation body having a mounting portion and a tongue depression portion adjacent the mounting portion, the body providing at least one airflow pathway therethrough;

maxilla and mandibular teeth engaging elements including teeth receiving portions, wherein the teeth engaging elements include a base plate mounted underneath floor portions of the respective teeth receiving portions, and wherein the each base plate includes oppositely disposed mounting flange members wherein the flange members are slidably received on the mounting portion of the body for selectively positioning the mandibular teeth engaging element relative to the maxilla teeth engaging element;

a tongue receiving member mounted to the maxilla teeth engaging element, wherein the tongue receiving member is disposed centrally of the mounting portion of the body and relative to the tongue depression means to provide support for the tongue; and wherein the mandibular teeth engaging element is slidably positioned on the mounting portion of the body forward of the maxilla element to locate the mandible forward of the maxilla and wherein the tongue depression means urges against a surface portion of a user's tongue, close to the throat to substantially maintain unobstructed airways.

In a third aspect of the present invention there is described an oral cavity manipulator including:

a foundation body having an upper and lower mounting portion, the upper and lower mounting portions being hingedly interconnected, and a tongue depression portion adjacent posterior mounting portions for urging against a surface of the tongue close to the user's throat, the body providing at least one airflow pathway therethrough;

a mandibular teeth engaging element having a teeth receiving portion, the mandibular teeth engaging element including a base plate mounted underneath a floor portion of the teeth receiving portion, and wherein the base plate includes oppositely disposed mounting flange members which are slidably received on the lower mounting portion of the foundation body;

a maxilla teeth engaging element having a teeth receiving portion, the maxilla teeth engaging element including a base plate mounted to a portion of the teeth receiving portion, and wherein the base plate includes oppositely disposed mounting flange members which are slidably received on the upper mounting portion of the body;

a tongue receiving member mounted to a forward portion of the maxilla teeth engaging element and disposed centrally of the body; and wherein the mandibular teeth engaging element is slidably positioned on the mounting portion of the body forward of the maxilla element to locate the mandible forward of the maxilla and wherein the tongue depression means urges against a surface portion of a user's tongue, close to the throat to substantially maintain unobstructed airways.

The body can be hollow and can include at least one outlet rearwardly of the body for egress of air following transfer of air from the forward opening through the body upon a breathing intake cycle. The foundation body allows passage air through an inlet forwardly of the body and exiting outlet openings in the tongue depression means. One advantage of this arrangement is that the sufferer's oral cavity is less prone to dryness. The forward inlet can be shaped to receive a connection to an air pump.

The tongue receiving means can include a flange extending adjacent to or from a front portion thereof, wherein the flange includes a series of spaced openings for receiving cooperating mounting members located on a forward portion of the maxilla teeth engaging element.

The teeth engaging elements can include mounting structures for receiving forward portions of respective base plates.

In a fourth aspect of the invention there is described a method of substantially preventing or at least minimising incidences of OSA and/or snoring, the method including:

providing a device which can be inserted within the oral cavity of a user/sufferer, the device having a body having an upper and lower mounting portion, the upper and lower mounting portions being hingedly interconnected, and a tongue depression portion adjacent the mounting portions for urging against a surface of the tongue close to the user's throat, the body providing at least one airflow pathway therethrough;

a mandibular teeth engaging element having a teeth receiving portion, the mandibular teeth engaging element including a base plate mounted to a portion of the teeth engaging element opposite the teeth receiving portion, and wherein the base plate includes oppositely disposed mounting flange members which are slidably received on the lower mounting portion of the body;

a maxilla teeth engaging element having a teeth receiving portion, the maxilla teeth engaging element including a base plate mounted to a portion of the teeth engaging element opposite the teeth receiving portion, and wherein the base plate includes oppositely disposed mounting flange members which are slidably received on the upper mounting portion of the body;

a tongue receiving member mounted to a portion of the maxilla teeth engaging element and disposed centrally of the body; and wherein the method includes fitting the manipulator within the oral cavity, such that the mandibular teeth engaging element is slidably positioned on the mounting portion of the body forward of the maxilla element to locate the mandible forward of the maxilla and the tongue depression means urges against a surface portion of a user's tongue, close to the throat to substantially maintain unobstructed airways.

In a further related aspect of the present invention there is provided an improved oral cavity manipulator including:

a substantially longitudinal planar body having a mounting portion, the body having an air inlet and outlet and at least one airflow pathway therebetween;

maxilla and mandibular teeth engaging elements including teeth receiving portions, wherein the teeth engaging elements are adapted to be adjustably received on the mounting portion of the body so that the maxilla and mandibular elements can be selectively positioned relative to each other, wherein in an operating condition the mandibular teeth engaging element is adjustably located on the mounting portion of the body forward of the maxilla element to locate the mandible forward of the maxilla to substantially maintain unobstructed airways.

Compared to prior art devices the improved oral cavity manipulator allows adjustment of the mandibular element relative to the maxilla element thus to reposition the mandibular of a wearer and assist maintaining airways in an open condition.

The improved oral cavity manipulator can include a tongue receiving structure. The tongue receiving structure can be mounted to an underneath portion of the maxilla teeth engaging element.

The maxilla and mandibular teeth engaging elements can include a base plate mounted to portions of the respective teeth engaging elements opposite the teeth receiving portions. The each base plate includes oppositely disposed mounting flange members wherein the flange members can be slidably received on the mounting portion of the body. The maxilla and mandibular teeth engaging elements can be mounted to the mounting portions of the body such that the teeth engaging elements can be altered to suit the shape of a user's oral cavity.

In a further embodiment there is described an oral cavity manipulator for controlling the position of tongue and jaw, the manipulator including:
a foundation body
maxilla and mandibular teeth engaging elements mountable on the foundation body and having width equal to or greater than the width of the foundation body and including teeth receiving portions for in use receiving the teeth of the user,
a tongue position means attached to one of the foundation body, or the teeth engaging elements
wherein in an operating condition the mandibular teeth engaging element is selectively located on the foundation body forward of the maxilla teeth engaging element to receive and locate the mandible of a user forward of the maxilla and position the tongue between the teeth elements to substantially maintain unobstructed airways at the throat or the user.

The foundation body can include a mounting means such that the positioning of the mandibular teeth engaging element and/or the maxilla teeth engaging element is adjustable by the mounting means.

The mandibular teeth engaging element can be hingedly mounted so that in use the mandibular teeth engaging element moves relative to the maxilla teeth engaging element when a user opens his/her mouth. The mandibular teeth engaging element can be mounted to the foundation body. Alternatively, the mandibular teeth engaging element can be mounted on the maxilla teeth engaging element.

In a further embodiment there is described an oral cavity manipulator according to any one of the preceding claims for controlling tongue and jaw positioning, the manipulator including:
the foundation body being an elongated body having at least one mounting portion, the body having an air inlet and outlet and at least one airflow pathway therebetween;
the maxilla and mandibular teeth engaging elements having width equal to or greater than the width of the substantially longitudinal body and including teeth receiving portions, wherein the teeth engaging elements are adapted to be selectively mounted on the mounting portion of the body to allow the selective positioning of the maxilla and mandibular teeth engaging elements relative to each other,
wherein in use the mandibular teeth engaging element is selectively located on the mounting portion of the body forward of the maxilla element to receive and locate the mandible of a user forward of the maxilla and position the tongue between the teeth elements to substantially maintain unobstructed airways at the throat of the user.

The tongue receiving structure can be mounted to a portion of the maxilla teeth engaging element or the foundation base and wherein the tongue receiving structure provides a cavity for receiving a front part of the tongue in at least partially vacuum mode.

In use the tongue depression portion extends below the plane of the body to apply a force against a base portion of a user's tongue close to the throat to urge the tongue down and forward and thereby substantially maintain unobstructed airways. The tongue receiving structure can be integral with the foundation base.

The oral cavity manipulator can further include a pair of oppositely disposed flange elements located adjacent the tongue depression means to laterally urge against curtain portions of the throat of a wearer.

In a further embodiment there is disclosed an oral cavity manipulator including:
a foundation body having a mounting portion and a tongue depression portion adjacent the mounting portion, the body providing at least one airflow pathway therethrough;
maxilla and mandibular teeth engaging elements including teeth receiving portions, wherein the teeth engaging elements are adapted to be adjustably received on the mounting portion of the body so that the maxilla and mandibular elements can be selectively positioned relative to each other,
wherein in an operating condition the mandibular teeth engaging element is adjustably positioned on the mounting portion of the body forward of the maxilla element to locate the mandible forward of the maxilla and wherein the tongue depression means urges against a surface portion of a user's tongue, close to the throat to substantially maintain unobstructed airways.

The tongue depression portion can be adjustable with respect to the plane of the mounting portion of the body to apply a suitable effective force against the base portion of a user's tongue to displace the tongue away from an airway obstructing position. The tongue depression portion includes a removable sheath.

The foundation body can include two spaced parallel arms along which the maxilla and mandibular teeth engaging elements can be slidably received. The arms can be tubular so as to provide an airflow pathway therethrough. Even further, the arms can include a series of spaced openings forming the mounting portion for receiving and selectively positioning the maxilla teeth engaging element in one of said openings. The foundation body is integral to the teeth engaging elements.

The maxilla and mandibular teeth engaging element can include a base plate mounted by the respective teeth receiving portion. The base plate can be located underneath floor portions of the teeth receiving portions.

The maxilla teeth engaging element can include a pair of symmetric mounting flange members dependent from the base plate, wherein the maxilla teeth engaging element is adapted to be slidably received on the mounting portion of the foundation body by the flange members, and wherein the flange members include a locking pin which cooperate with any one of the spaced openings in the arms of the foundation body to allow selective positioning of the maxilla teeth engaging element on the foundation base.

The maxilla teeth engaging element can further include a pair of hinge plates symmetrically disposed and dependent from the base plate, wherein the hinge plates include a plurality of hinged locations to allow selective hinged positioning of the mandibular teeth engaging element one of the hinged locations.

The mandibular teeth engaging element can include a further pair of symmetric mounting flange members dependent from the base plate, wherein the flange members include a locking pin which cooperate with any one of the plurality of hinged locations on the hinge plates so that in use the mandibular teeth engaging element pivots relative to the maxilla teeth engaging element when a user opens his/her mouth.

The base plate can be located within teeth receiving portions of the teeth engaging elements, and wherein the base plate further includes an adjustment means, which allows lateral adjustment of the teeth receiving portions.

The oral cavity can further include a releasable locating member having complementary mating components that locate the position of the maxilla teeth engaging element in a selective position relative to the mandibular teeth engaging element.

The releasable locating member can include a first locating member being adjustably mounted to the maxilla teeth engaging element or foundation body in a selective location, and a second locating member mounted to the mandibular teeth engaging element or foundation base, wherein the first and second locating members are adapted to cooperate such that in use the mandibular teeth engaging element is able to open with corresponding jaw movement and maintain the relative location of the lower jaw with respect to the upper jaw when a user's mouth is closed.

The first and second locating members can be located adjacent anterior portions of the teeth engaging elements or foundation body.

The releasable locating member can include:
one or more saddle(s) located on a top surface portion of the foundation base, the one or more saddles including a seat for slidably receiving anterior portions of the maxilla teeth engaging element, the seat ending in a stop member
one or more adjustable locking structures selectively located on outside wall portions of the maxilla teeth receiving portions adapted to cooperate with the stop member to locate the maxilla teeth engaging element in a selected position on the foundation base whereby the anterior portions of the maxilla teeth engaging element are slidably received by the seat and the maxilla teeth engaging element is located in a selected position on the foundation base when the locking structure abuts the stop member.

In a further embodiment there is described an improved oral cavity manipulator for use in substantially preventing incidences of OSA or snoring, the manipulator including:
a body having a mounting portion and a tongue depression portion adjacent the mounting portion, the body providing at least one airflow pathway therethrough;
maxilla and mandibular teeth engaging elements including teeth receiving portions,
wherein the teeth engaging elements include a base plate mounted to portions of the respective teeth engaging elements opposite the teeth receiving portions, and wherein the each base plate includes oppositely disposed mounting flange members wherein the flange members are slidably received on the mounting portion of the body for selectively positioning the mandibular teeth engaging element relative to the maxilla teeth engaging element;
a tongue receiving member mounted to the maxilla teeth engaging element, wherein the tongue receiving member is disposed centrally of the mounting portion of the body and relative to the tongue depression means to provide support for the tongue; and
wherein the mandibular teeth engaging element is slidably positioned on the mounting portion of the body forward of the maxilla element to locate the mandible forward of the maxilla and wherein the tongue depression means urges against a surface portion of a user's tongue, close to the throat to substantially maintain unobstructed airways.

In yet a further embodiment of the present invention there is described an oral cavity manipulator including:
a foundation body having a mounting portion for receiving maxilla and mandibular teeth engaging elements, the mourning portion comprising an upper and lower platform mounting portions being hingedly interconnected, and a tongue depression portion adjacent the mounting portions for urging against a surface OF the tongue close to the user's throat, the body providing at least one airflow pathway therethrough;
a mandibular teeth engaging element having a teeth receiving portion, the mandibular teeth engaging element including a base plate mounted to a portion of the teeth engaging element opposite the teeth receiving portion, and wherein the base plate includes oppositely disposed mounting flange members which are slidably received on the lower mounting portion of the body;
a maxilla teeth engaging element having a teeth receiving portion, the maxilla teeth engaging element including a base plate mounted to a portion of the teeth engaging element opposite the teeth receiving portion, and wherein the base plate includes oppositely disposed mounting flange members which are slidably received on the upper mounting portion of the body;
a tongue receiving member mounted to a portion of the maxilla teeth engaging element and disposed centrally of the body; and
wherein the mandibular teeth engaging element is slidably positioned on the mounting portion of the body forward of the maxilla element to locate the mandible forward of the maxilla and wherein the tongue depression means urges against a surface portion of a user's tongue, close to the throat to substantially maintain unobstructed In order that the invention be more readily understood the following detailed description is provided with reference to the accompanying drawings.

Figure 1:
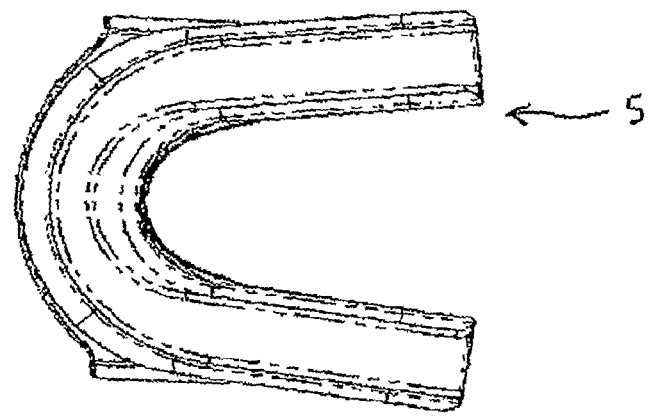
FIG. 1 is a top plan view of maxilla teeth engaging element in accordance with one embodiment of the present invention.
Figure 2:
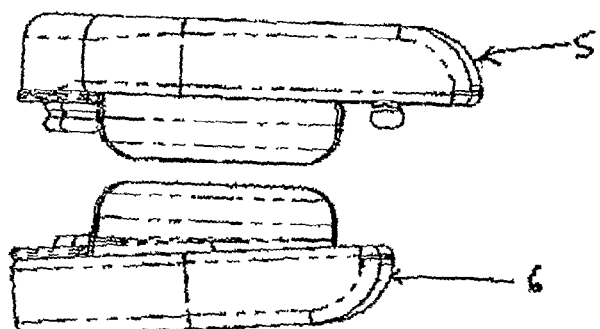
FIG. 2 is a side elevation of top plan view of maxilla and mandibular teeth engaging elements in accordance with one embodiment of the present invention.
Figure 3:
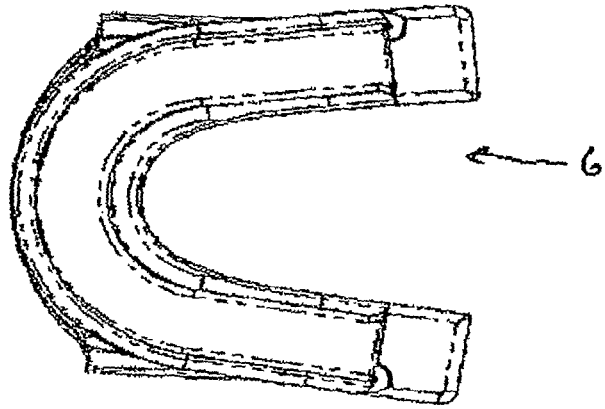
FIG. 3 is a top plan view of mandibular teeth engaging element in accordance with one embodiment of the present invention.
Figure 4:
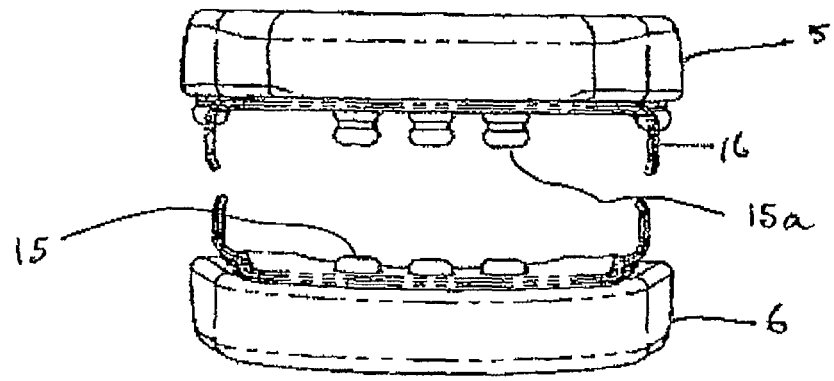
FIG. 4 is a front perspective view of maxilla and mandibular teeth engaging elements in accordance with FIG. 2.
Figure 5:
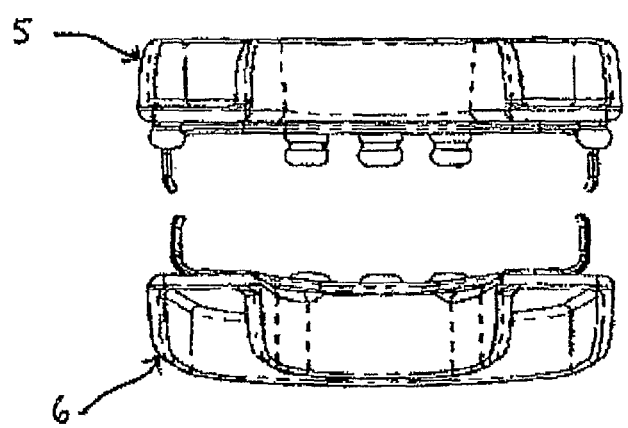
FIG. 5 is a rear perspective view or maxilla and mandibular teeth engaging elements in accordance with FIG. 2.
Figure 6:
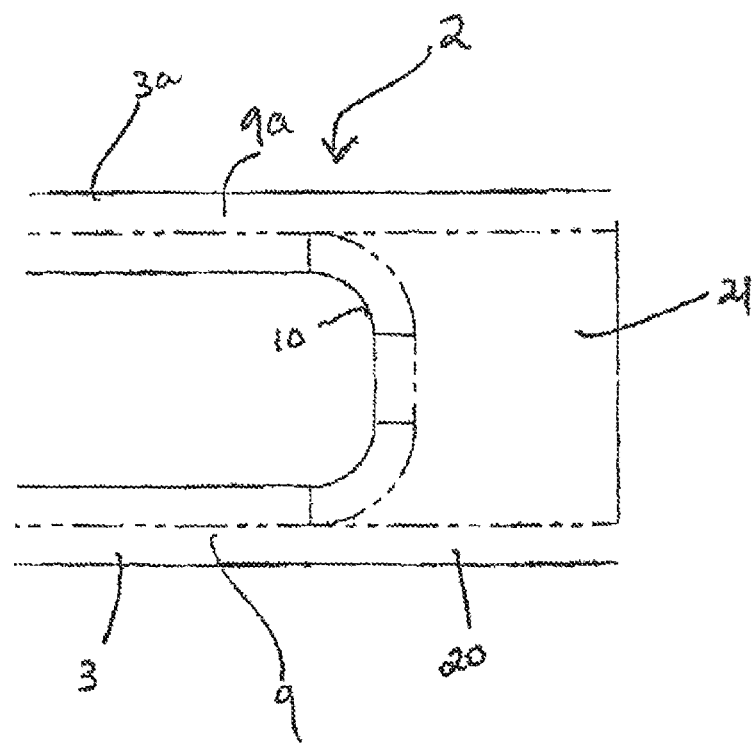
FIG. 6 is a plan view of the body portion of the improved oral cavity manipulator.
Figure 7:
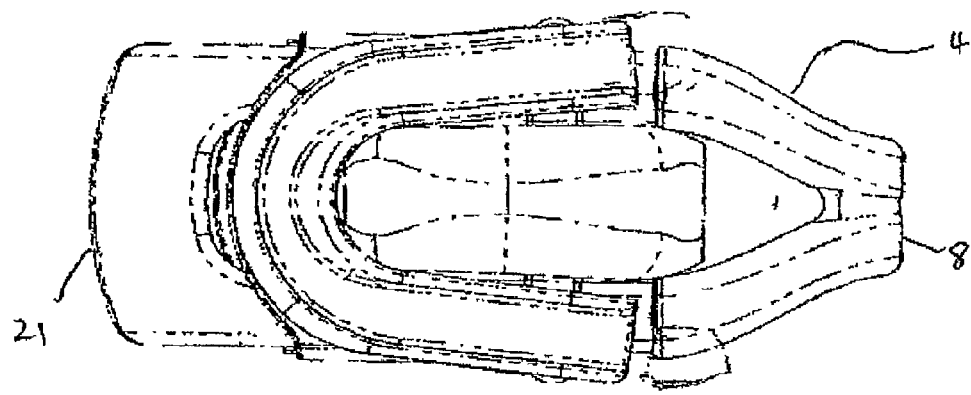
FIG. 7 is a top plan view of an improved oral cavity manipulator in accordance with one embodiment of the present invention.
Figure 8:
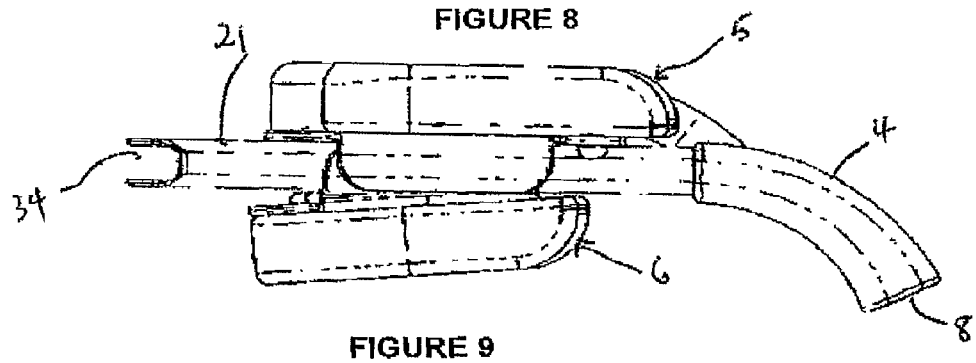
FIG. 8 is a cross-sectional view from side elevation of the improved oral cavity manipulator shown in FIG. 7.
Figure 9:
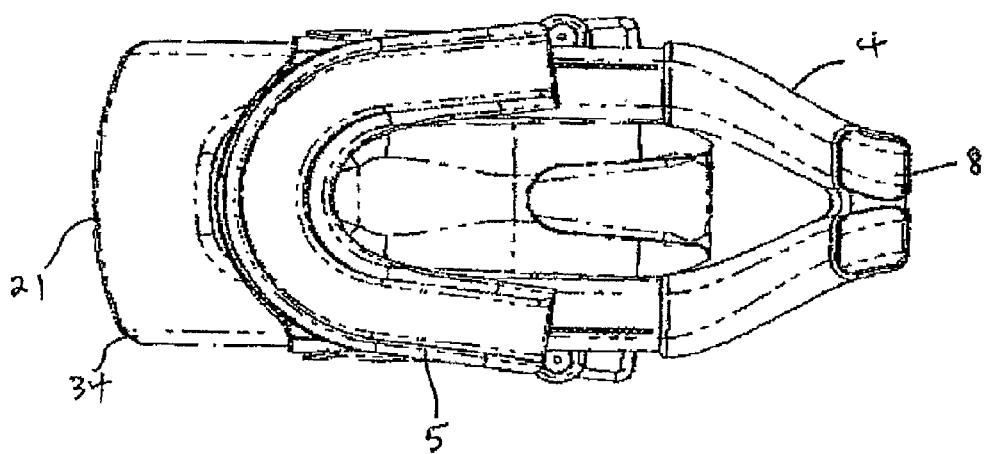
FIG. 9 is a plan view (underneath elevation) of the improved oral cavity manipulator of FIGS. 7 & 8

DETAILED DESCRIPTION OF THE PREFERRED EMBODIMENT WITH REFERENCE TO THE ACCOMPANYING DRAWINGS

Referring to FIGS. 1 to 6 there is shown an oral cavity manipulator, which includes a foundation body comprising an elongate planar body 2 (best seen in FIG. 6) having a mounting portion 3 and 3a for receiving maxilla (upper) 5 and mandibular (lower) 6 teeth engaging elements. The body has an air inlet 34 and air outlet 35 defining at least one airflow pathway through the body. The teeth engaging elements are adapted to be adjustably mounted on the mounting portions of the body to allow selective positioning of the maxilla and mandibular teeth engaging elements relative to each other.

The maxilla and mandibular teeth engaging elements include (i) teeth receiving portions of a generally u-shaped structure having a floor and dependent wall forming a cross-sectional u-shaped recess for receiving teeth therein, and (ii) a base plate 13 and 13a mounted underneath floor portions of the respective teeth receiving portions.

Each base plate includes a flange element 14. The flange elements include spaced openings to receive bosses 15 and 15a. Bosses 15 and 15a are received in respective openings to secure the maxilla and mandibular teeth engaging elements to the base plates. The base plates also include spaced wall members 16 adapted to be received on the mounting portions 3 and 3a of the body in an adjustable condition such that the position of the teeth engaging elements can be altered for example to advance the mandibular. A particular advantage of the present invention is that it provides a hitherto unknown adjustability of the maxilla and mandibular teeth engaging elements to allow a treatment of sleep apnoea by mandibular advancement.

Referring to the FIGS. 7 to 12 there is shown a further embodiment of the oral cavity manipulator 1 in accordance with the present invention. The oral cavity manipulator 1 includes a foundation body 2 (best seen in FIG. 11) having a mounting portion 3,3a and a tongue depressing portion 4 located rearwardly of the mounting portion. The oral cavity manipulator further includes a maxilla 5 and mandibular 6 teeth engaging elements mounted to the mounting portions of the body in a slidable condition so that at least the mandibular element 6 is moveable relative to the maxilla element 5 to allow advancement of the mandibular.

Figure 11:
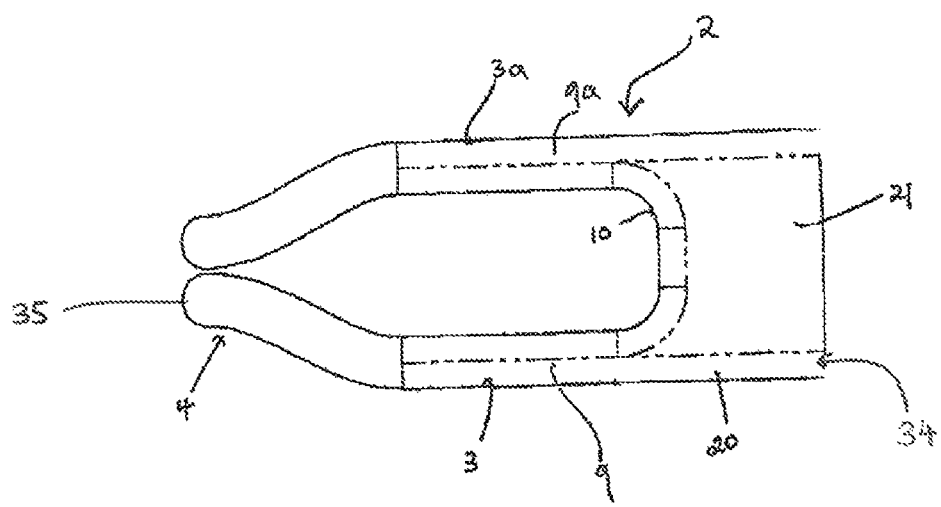
FIG. 11 is a plan view of the body portion of the improved oral cavity manipulator.
Figure 12:
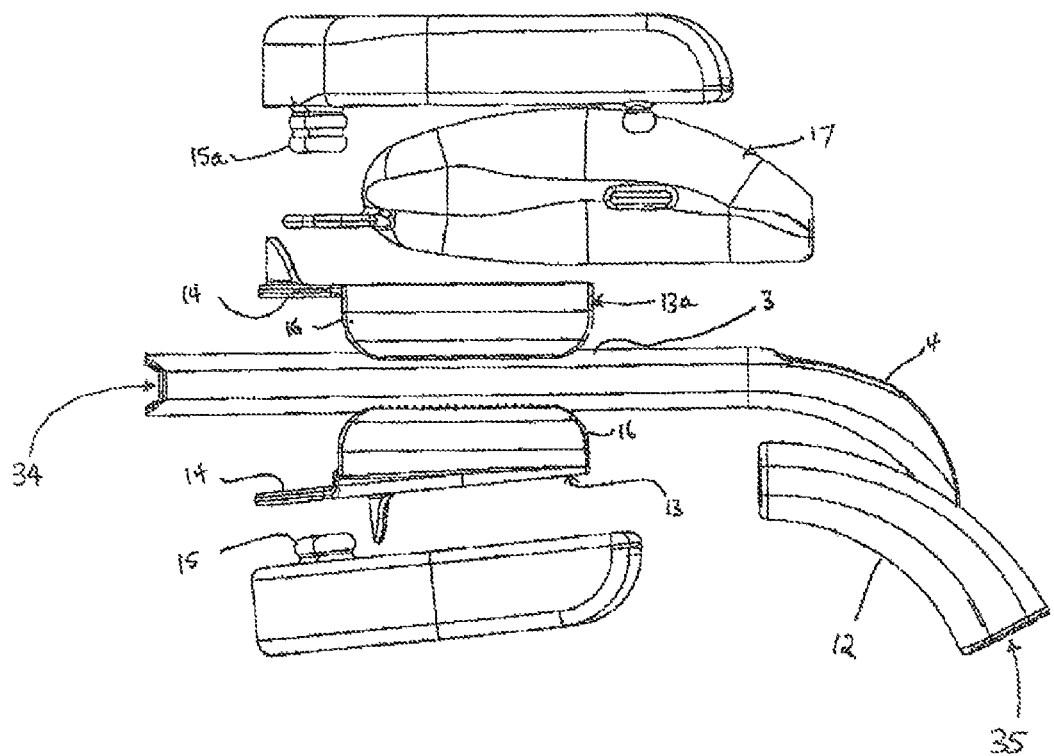
FIG. 12 is a side view of the improved oral cavity manipulator of FIGS. 7 to 11 in various stages of assembly.

Referring to FIGS. 11 and 12, the body includes an air inlet 34 leading to an airflow passage 20 extending the length of the body. The tongue depression portion 4 is hollow allowing continuous passage of air through the body and includes air outlet 35, the body defining at least one airflow pathway therethrough.

In FIG. 11 the body has spaced parallel arms 9 and 9a, which define the mounting portion 3 of the body. The arms 9 and 9a are at least partially hollow along their length and interconnected by a bridge 10 which together define a u-shaped structure. The body includes a connecting structure 21 forwardly of the bridge for connecting to an external air pump, and provides a first airflow pathway in fluid connection with the hollow section of the mounting portion. The tongue depression portion 4 is also hollow and in fluid connection with the hollow section of the mounting portion to allow airflow throughout the body. The body is substantially rigid and fabricated from polymeric materials The tongue depression portion 4 curves away from and terminates below the plane of the foundation body such that it urges against a base portion of a wearer's tongue to substantially prevent blockage of airways by collapse of the tongue. The tongue depression portion is generally v-shaped and includes a sheath 12 of soft material, which cushions the contact with the tongue.

In one embodiment (not shown) the tongue depression portion can be adjusted relative to the longitudinal plane of the body to alter the force applied to the base tongue. The tongue depression means further includes oppositely disposed flange elements (not shown) located adjacent the tongue depression means for urging against curtain portions of the throat of a user. Without being bound by theory, the flange elements help to prevent collapse of the curtain portions of the throat by providing a lateral force while simultaneously depressing and displacing the tongue forward.

The mounting portion 3 of the body includes a series of spaced apart openings on top and opposite surfaces for releasably receiving interlocking elements on base portions of the teeth engaging elements and thereby to allow adjustable positioning of the teeth engaging elements thereon.

As best seen in FIG. 12 the maxilla and mandibular teeth engaging elements include a base plate 13a and 13 mounted to underneath portions of the respective teeth engaging elements. The each base plate includes flange elements 14. The flange elements include spaced openings to receive bosses 15 and 15a. Bosses 15 and 15a are received in respective openings to secure the maxilla and mandibular teeth engaging elements to the base plates. The base plates also include spaced wall members 16 adapted to be received on the mounting portion of the body in an adjustable condition such that the position of the teeth engaging elements can be altered for example to advance the mandibular. A particular advantage of the present invention is that it provides a variety of different ways of treating sleep apnoea. It is also particularly advantageous and not known previously to provide a combination of (i) mandibular advancement, and (ii) tongue depression.

Figure 10:
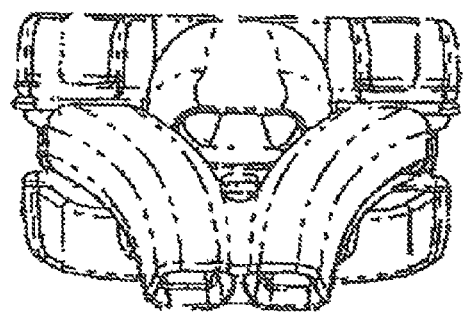
FIG. 10 is a rear perspective view of the improved oral cavity manipulator of FIGS. 7 to 9

As seen in FIGS. 10 and 12, the oral cavity manipulator further includes a tongue receiving structure 17. The tongue receiving structure is mounted to a portion of the maxilla teeth engaging element and resides within the recess defined by the u-shaped structure of the maxilla teeth engaging element and adjacent the tongue depression portion. The tongue receiving structure includes an internal chamber 38, which in use receives the wearer's tongue. The tongue receiving structure includes a shoulder portion 18 having a plurality of spaced openings therein to receive mating boss elements 15a on a forward portion of the maxilla teeth engaging element. Further, to secure the tongue receiving structure, the maxilla element includes a boss 39 rearwardly positioned to be received within opening 40. It is understood that a wearer's tongue when received within the internal housing is retained therein by result of a vacuum created as air escapes from a forward portion and the tongue forms a seal. This action assists in maintaining the tongue in a forward position.

Figure 13:
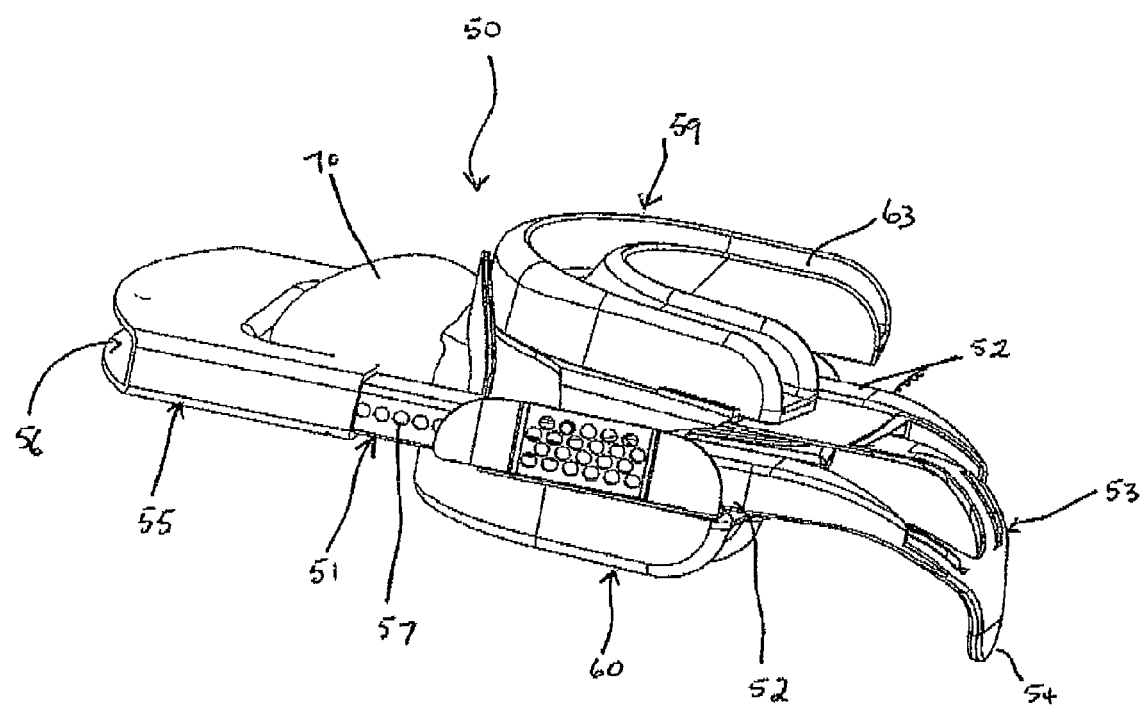
FIG. 13 is a perspective view of a further embodiment of the present invention shown in an assembled form.

Turning to FIG. 13 there is shown an oral cavity manipulator device 50 including a foundation body 51 of generally planar configuration comprising two parallel arms 52. Posterior region of the arms 52 are integrally joined by a tongue depressing member 53 of general u-shape. The tongue depressing member 53 extends downwardly in an arcuate manner from the plane of the spaced arms 52 and terminates in a tongue contact member 54, which in use positively depresses a base portion of a user's tongue and urges the tongue forwardly within the oral cavity to help maintain open airways.

Anterior ends of the arms 52 of the foundation body are interconnected by a connecting member 55. The connecting member 55 is shown as a separate component in FIG. 13 interconnecting ends of arms 52. In FIG. 13 both the arms 52 and connecting structure 55 are tubular, and connecting member 55 includes an opening 56 for ingress of air. When the connecting member is assembled as in FIG. 13 the connecting member and arms provide dual airflow pathways between the anterior and posterior region of the foundation body 51. In use the opening 56 of the connecting member 55 extends proud of a user's mouth so that air can be transferred and directed from the opening 56 through the airflow pathways exiting the posterior region close to a user's throat.

As shown, the tongue depressing member 53 is integrally molded to the arms 52 so that the posterior region of the foundation body is substantially rigid while being lightweight. The connecting member 55 also provides structural support for the arms 52 and strengthens the rigidity of the foundation body. The tubular arms further include a series of spaced openings 57 on an outside section of the arms, which receive a mating pin 58 (best seen in FIG. 14) to allow selective positioning of an upper (maxilla) teeth engaging element 59 on the foundation body relative to the tongue contact member 54.

The foundation body is made from a plastics material selected from thermoplastic and thermosetting polymers including but limited to PVC, polypropylene, polyethylene but not limited thereto. For instance the foundation base can be fabricated from a metal.

Figure 14:
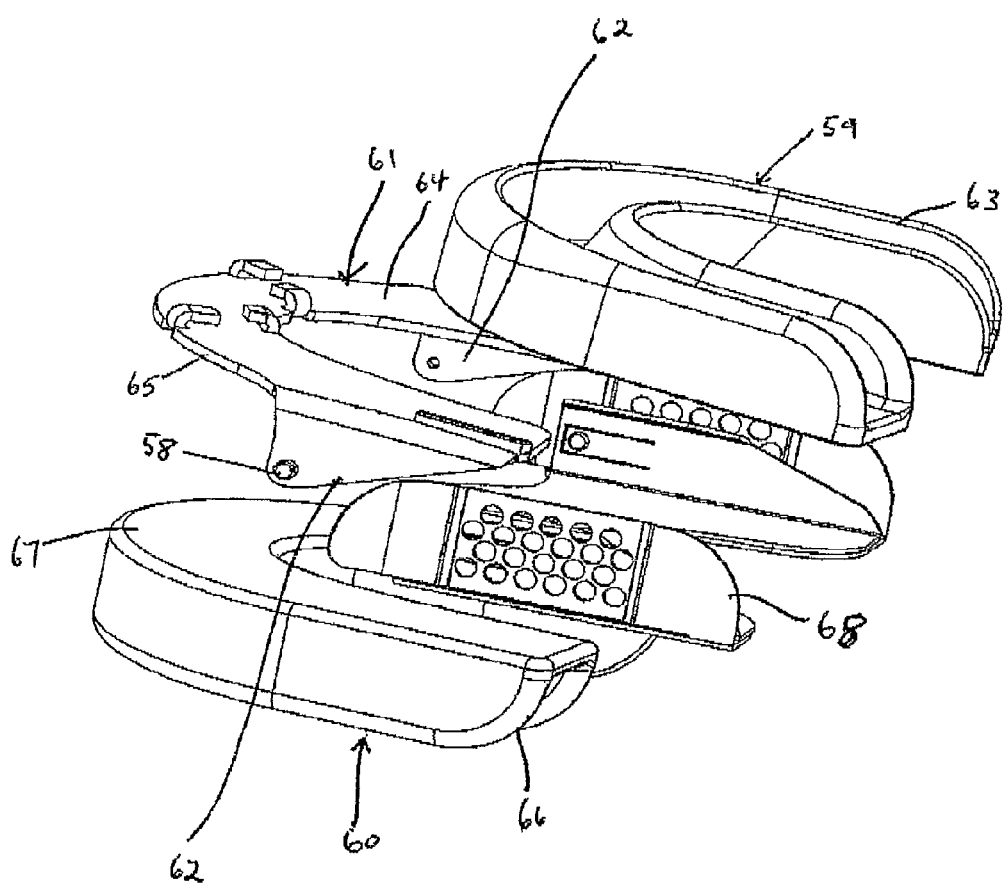
FIG. 14 is a perspective view of part of the embodiment shown in FIG. 13 showing relative positioning of at least some of the elements.

As shown in FIG. 14, the oral cavity device 50 includes an upper (Maxilla) 59 and lower (mandibular) 60 teeth engaging elements. As shown in FIG. 13 the upper teeth engaging plate in assembled form is mounted on an upper section of the arms 52 and adapted to slide along the foundation body to allow selective adjustment. The upper teeth engaging element 59 includes a teeth receiving portion 63 which is generally u-shaped having a u-shaped cross-section for receiving a user's upper teeth. The upper teeth receiving portion 63 is mounted on a base plate 61.

The base plate 61 includes a planar platform 64 defined by an upper and lower surface separated by an edge 65. The platform is shaped to the configuration of the teeth receiving portion 63 and the upper surface of the platform is fixed underneath the teeth receiving portion. The base plate includes a pair of flange elements 62 which extend from a rear portion of the platform from edge 65 downwardly below the plane of the platform 64.

The flange elements 62 include a pin 58 disposed on an internal facing surface thereof which cooperate with openings 57 in the arms 52 to allow selective positioning of the upper teeth engaging element 59 relative to the tongue contact member 54. To assist retain the upper teeth engaging element 59 on the foundation body the flange elements 62 include a curved end (not shown) which embrace an underneath portion of the arms 52 in slidable condition.

The lower teeth engaging element 60 includes a teeth receiving portion 66 for receiving lower teeth of a user, and a base plate (not shown) attached to the roof portion 67 of the teeth receiving portion 66. The base plate includes oppositely disposed a flange elements having a locking pin for selective location on a hinge plate 68.

In FIGS. 13 and 14 the upper teeth engaging element 59 includes a further pair of symmetric hinge plates 68 dependent from the base plate 61 located on the outside the flange elements 62. The hinge plates 68 include a plurality of hinged locations 69. The locking pin is adapted to cooperate with any one of the plurality of hinged locations 69 on the hinge plates so that in use the mandibular teeth engaging element pivots relative to the maxilla teeth engaging element when a user opens his/her mouth.

FIG. 13 further shows a tongue receiving structure 70. The tongue receiving structure is mounted to a forward portion of the maxilla teeth engaging element or the foundation base and provides an opening leading to an internal chamber for receiving a front part of the tongue. As a user's tongue is inserted within the chamber of the tongue receiving structure air is displaced outwardly thus creating a partial vacuum, which helps to retain the user's tongue in a forward position.

Figure 15:
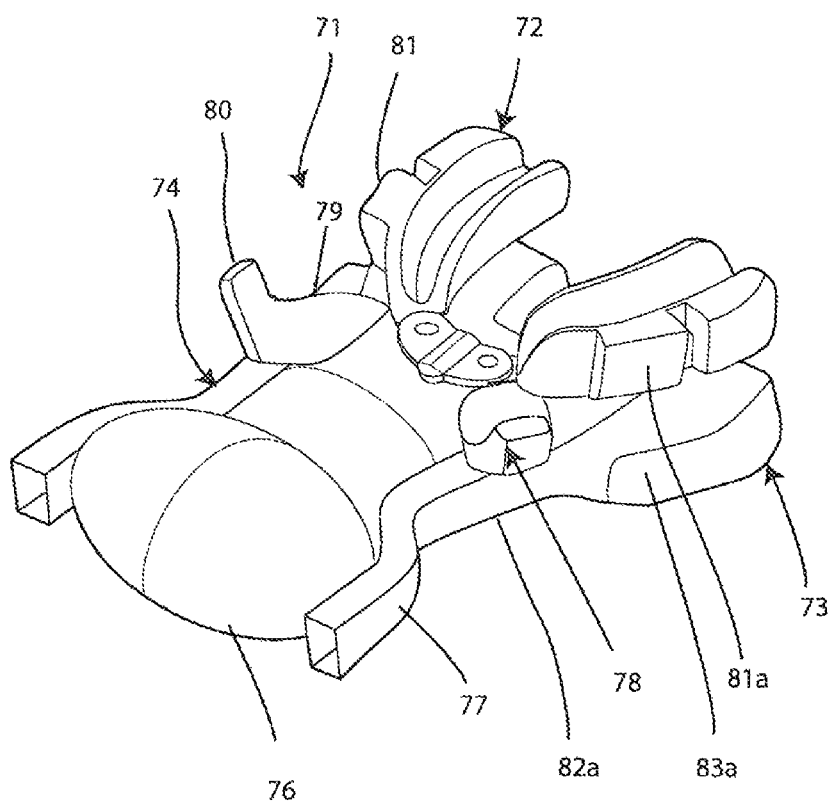
FIG. 15 is a perspective view of a further embodiment of the present invention in an assembled form.
Figure 16:
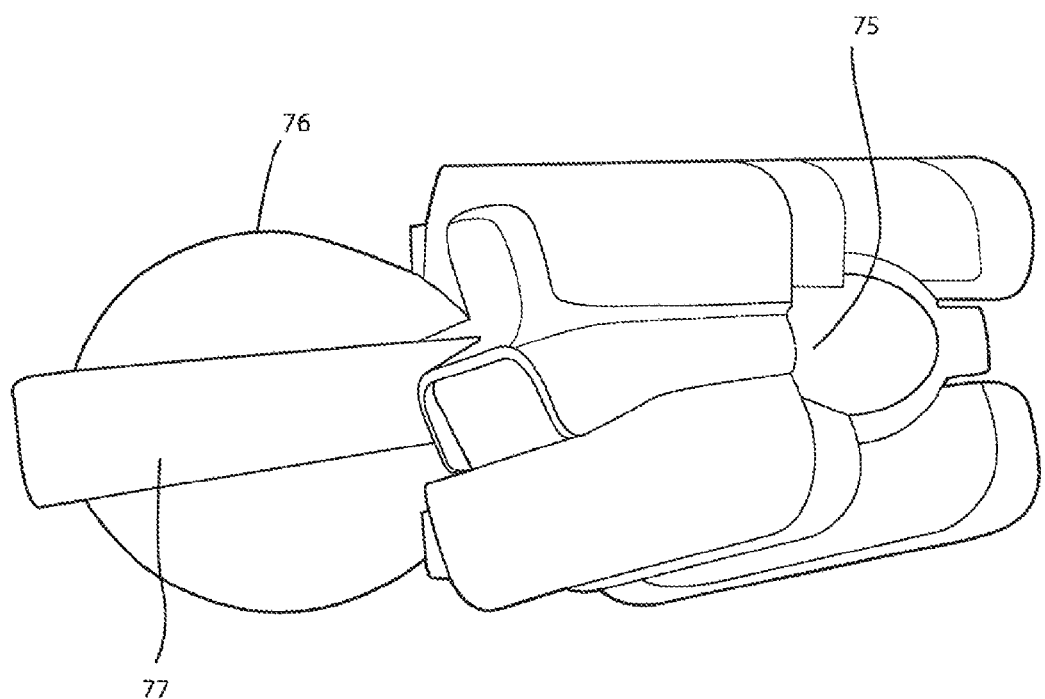
FIG. 16 is a side perspective view of the device in FIG. 15 in an assembled form.

Now referring to FIG. 15, there is shown a further embodiment of the present invention in which an oral cavity device 71 includes an upper 71 and lower 73 teeth engaging elements mounted to a foundation body 74. As best shown in FIG. 16, the foundation body 74 includes an internal elongate chamber 75 with an opening at one end for receiving the tongue of a user within the chamber. The chamber 75 further includes a bulbous closed end 76 opposite the opening to create a partial vacuum when the user's tongue is inserted in the chamber so as to retain the tongue in a forward position. The chamber thus helps to substantially avoid the tongue from inadvertently falling back towards the throat of a wearer thus potentially blocking passage of air.

The foundation body 74 includes a pair of oppositely disposed hollow conduits 77 integrally formed on external side portions of the chamber 75. The hollow conduits provide an airflow pathway for passage of air from the user's mouth to a position adjacent the throat or posterior teeth.

As best seen in FIG. 15, the oral cavity manipulator further includes a releasable locating member having complementary mating components that locate the position of the maxilla teeth engaging element in a selective position relative to the mandibular teeth engaging element. In this embodiment the releasable locating member includes oppositely disposed saddles 78 on an upper section thereof for receiving anterior portions of the upper teeth-engaging element 72 in sliding relation. The saddles 78 include a seat 79 and a stop member 80 extending upwardly at an angle from the seat. The stop member(s) are adapted to cooperate with adjustable wedge-shaped sections 81 and 81a on the upper teeth engaging element.

Figure 19:
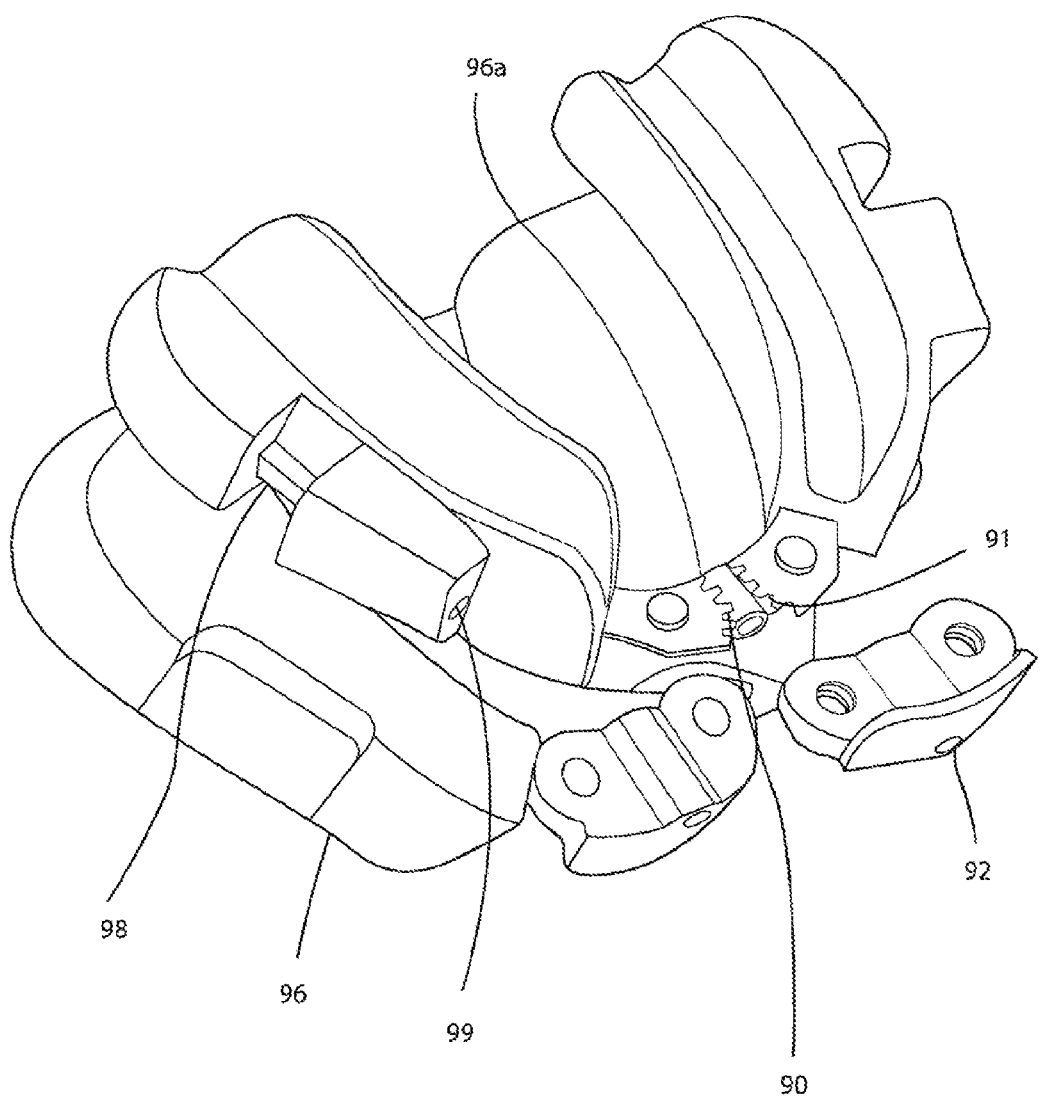
FIG. 19 is a perspective view of upper and lower teeth engaging elements in FIG. 18 shown in partially assembled form.

The wedge-shaped sections 81 and 81a are selectively adjustable along the length of the outside wall of the upper teeth receiving portion. As best seen in FIG. 19, the wedge-shaped sections are interconnected to a rearward block structure 97 and 97a via a screw adjustment means 98. The wedge-shaped members have an internal threaded section and receive mating threaded section of a screw. The screw extends into rearward block structure 97 and turning the screw at access point 99 allows selective positioning of the wedge-shaped member thereby to adjust the relative position of the upper and lower teeth engaging members in use.

The foundation body also includes inverted u-shaped recesses 82 and 82a immediately adjacent and underneath the saddles to cooperate with upstanding flange members 83 and 83a on opposite sides of the lower teeth engaging element.

Figure 17:
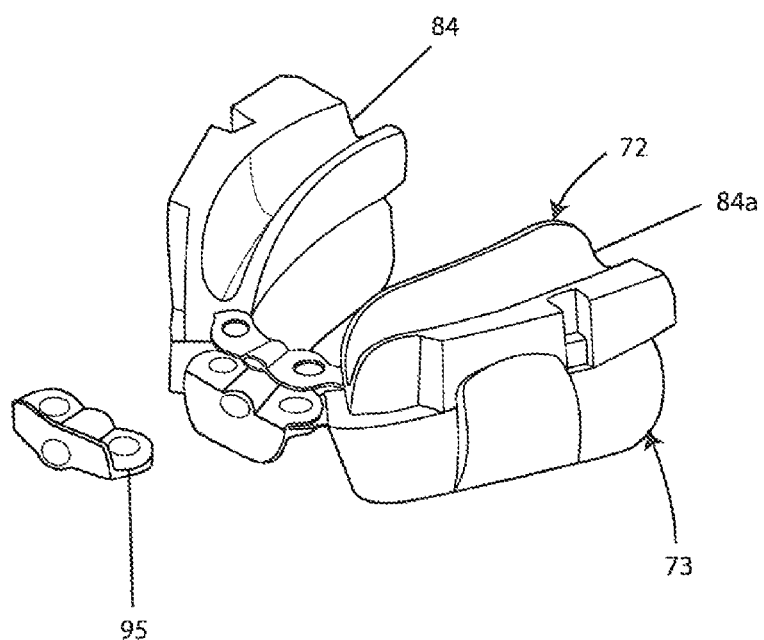
FIG. 17 is a perspective view of upper and lower teeth engaging elements as shown in FIGS. 15 and 16.
Figure 18:
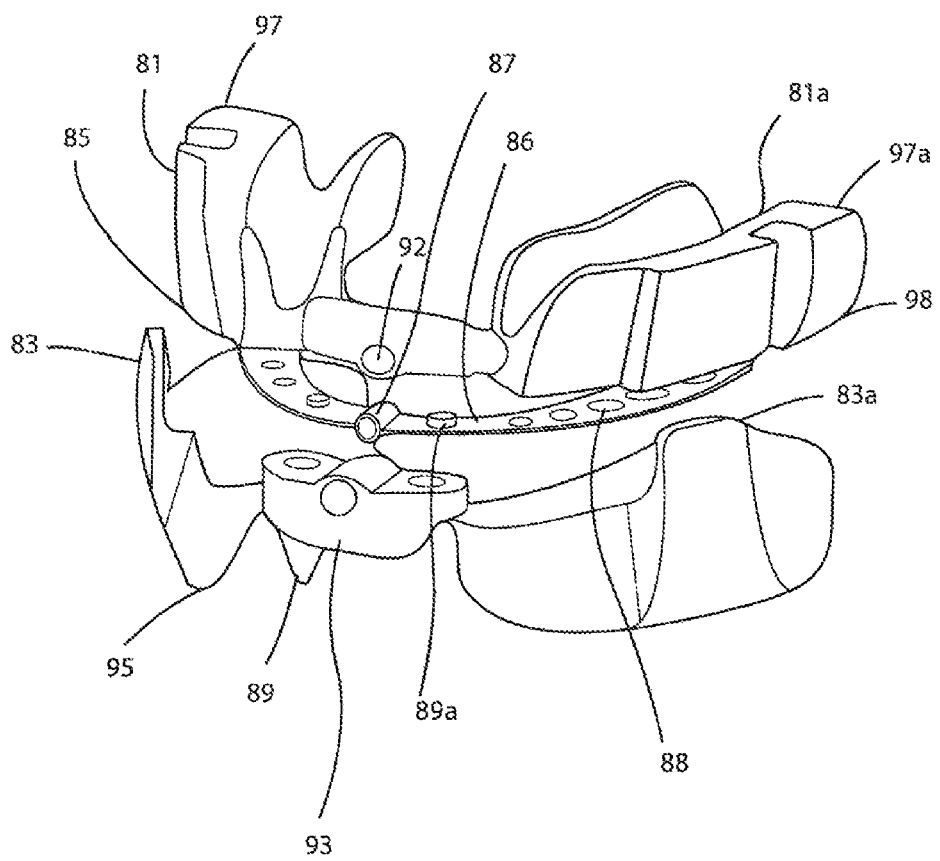
FIG. 18 is a front perspective view of upper and lower teeth engaging elements in FIG. 17;
plan view of upper and lower teeth engaging plates juxtaposed for fitting location relative to the central or body portion shown in FIG. 17.

Referring to FIGS. 17 to 19 there is shown a construction of the upper 72 and lower 73 teeth engaging elements used in this embodiment of the invention. Firstly, the upper teeth engaging element 72 includes a pair of teeth receiving portions 84 and 84a of generally u-shaped cross-section. As seen in FIG. 18, the pair of upper teeth receiving portions includes openings 85 and contiguous internal passage therethrough. A base plate 86 is inserted through the respective openings 85 thereby operatively interconnecting the pair of teeth receiving portions 84 and 84a.

The plate 86 as best seen in FIG. 18 consists of two arcuate symmetric arms joined by a central connecting member 87. The two arms are shaped to substantially correspond to the base plate. Each of the arms include a series of spaced openings 88 and bosses 89 and 89a adjacent the connecting member. As best seen in FIG. 19, the arcuate arms and central connecting member include mating interlocking threads 90 and 91. The central connecting member is adapted to be turned by screw means 92. In operation, when the screw means is turned, the arcuate arm sections are displaced laterally to allow widening or narrowing of the relative positions of the teeth receiving portions. The upper teeth engaging element 72 further includes a cover plate 93, which provides a recess 94 for receiving anterior section of the base plate 86. The cover plate 93 further includes spaced openings 95 for receiving bosses 89 and 89a to secure the cover plate to the anterior section of base plate 86.

The lower teeth engaging element 73 includes a pair of teeth receiving portions 96 and 96a of generally u-shaped cross-section. As with the upper teeth receiving portions, the pair of lower teeth receiving portions includes openings and contiguous internal passage therethrough. A base plate is inserted through the respective openings thereby operatively interconnecting the pair of teeth receiving portions 96 and 96a.

As indicated, the lower teeth engaging element include upstanding flange members 83 and 83a on opposite sides of the lower teeth receiving portions. These upstanding flange members cooperate with inverted u-shaped recesses 82 and 82a to help maintain the lower teeth engaging element in position. To adjust the relative position of the upper and lower teeth engaging elements, the wedge-shaped members 81 and 81a on the upper teeth engaging element is selectively positioned by moving the wedge-shaped member, thereafter the wedge-shaped members are brought into abutment with the stop members, whereby the stop members act as a stop and locate the upper teeth engaging element on the foundation body. This procedure can be used to adjust the forward positioning of the lower jaw of a user.

The invention claimed is:

1. An oral cavity manipulator comprising:
a foundation body having a mounting portion, wherein the foundation body provides at least one airflow pathway therethrough for respiration through a mouth of a user when the user's mouth is closed about the foundation body;
a tongue depression portion adjacent to and rearward of the mounting portion of the foundation body, wherein the tongue depression portion is configured to, in use, apply a force against a base portion of a user's tongue close to the user's throat to urge the user's tongue down and forward and thereby substantially maintain unobstructed airways; and
maxilla and mandibular teeth-engaging elements comprising teeth-receiving portions, wherein at least one of the maxilla and mandibular teeth-engaging elements is/are adapted to be adjustably mounted on the mounting portion of the foundation body so that the maxilla and mandibular teeth-engaging elements can be selectively positioned relative to each other,
wherein:
the maxilla and mandibular teeth-engaging elements each comprise a base plate mounted by the respective teeth-receiving portion,
in an operating condition, the mandibular teeth-engaging element is positioned on the mounting portion of the foundation body forward of the maxilla teeth-engaging element to locate the user's mandible forward of the user's maxilla,
in use, the tongue depression portion urges against a surface portion of the user's tongue, close to the user's throat to substantially maintain unobstructed airways,
the mandibular and maxilla teeth-engaging elements comprise a pair of oppositely disposed mounting flange members dependent from each base plate;
the mandibular teeth-engaging element is adapted to be slidably adjustable on the mounting portion of the foundation body;
the foundation body comprises two spaced parallel arms along which at least one of the maxilla and mandibular teeth-engaging elements can be slidably received;
the two spaced parallel arms comprise a series of spaced openings forming the mounting portion; and
the mounting flange members comprise a locking pin that cooperates with any one of the series of spaced openings in the two spaced parallel arms to allow selective positioning of the mandibular teeth-engaging element on the foundation body.

2. The oral cavity manipulator of claim 1, wherein the tongue depression portion is adjustable with respect to a plane of the mounting portion of the foundation body to apply a suitable effective force against the base portion of the user's tongue to displace the user's tongue away from an airway obstructing position.

3. The oral cavity manipulator of claim 1, wherein the two spaced parallel arms are tubular so as to provide an airflow pathway therethrough.

4. The oral cavity manipulator of claim 1, wherein the mandibular teeth-engaging element comprises a complementary mating component adapted to be received within one of the spaced openings of the series of spaced openings for selectively positioning the mandibular teeth-engaging element therealong.

5. The oral cavity manipulator according to claim 1, wherein:
the mandibular teeth-engaging element further comprises a pair of hinge plates symmetrically disposed and dependent from the base plate of the mandibular teeth-engaging element;
the pair of hinge plates comprise a plurality of hinged locations; and
the flange members of the maxilla teeth-engaging element comprise a locking pin that cooperates with any one of the plurality of hinged locations on the pair of hinge plates to allow selective hinged positioning of the maxilla teeth-engaging element in one of the plurality of hinged locations and to allow rotation of the user's jaw when the user opens his/her mouth.

6. The oral cavity manipulator according to claim 1, wherein the maxilla and mandibular teeth-engaging elements provide a generally u-shaped structure having a floor and dependent wall forming a cross-sectional u-shaped recess for receiving teeth therein, and
wherein the cross-sectional u-shaped recess comprises an impression composition for creating an impression fitting for the user's upper and lower dental arch.

7. The oral cavity manipulator according to claim 1, further comprising a releasable locating member having complementary mating components that locate a position of the maxilla teeth-engaging element relative to the foundation body.

8. An oral cavity manipulator comprising:
a foundation body having a mounting portion, wherein the foundation body provides at least one airflow pathway therethrough for respiration through a user's mouth when the user's mouth is closed about the foundation body;
maxilla and mandibular teeth-engaging elements comprising teeth-receiving portions, wherein at least one of the maxilla and mandibular teeth-engaging elements is/are adapted to be adjustably mounted on the mounting portion of the foundation body so that the maxilla and mandibular teeth-engaging elements can be selectively positioned relative to each other; and
a releasable locating member having complementary mating components that locate a position of the maxilla teeth-engaging element relative to the foundation body;
wherein, in an operating condition, the mandibular teeth-engaging element is positioned on the mounting portion of the foundation body forward of the maxilla teeth-engaging element to locate the user's mandible forward of the user's maxilla, and
wherein the releasable locating member comprises:
one or more saddles located on a top surface portion of the foundation body, the one or more saddles comprising a seat for slidably receiving anterior portions of the teeth-receiving portions of the maxilla teeth-engaging element, the seat ending in a stop member; and
one or more locking structures located on outside wall portions of the teeth-receiving portions adapted to cooperate with the stop member to locate the maxilla teeth-engaging element in a selected position on the foundation body,
whereby the anterior portions of the maxilla teeth-engaging portions are slidably received by the seat and the maxilla teeth-engaging element is located in a selected position on the foundation body when the one or more locking structures abut the stop member.

9. An oral cavity manipulator comprising:
a foundation body having a mounting portion for receiving maxilla and mandibular teeth-engaging elements, and a tongue depression portion adjacent the mounting portion for urging against a surface of a user's tongue close to the user's throat, the foundation body providing at least one airflow pathway therethrough;
a mandibular teeth-engaging element having a teeth-receiving portion, wherein the mandibular teeth-engaging element comprises a base plate mounted to a portion of the mandibular teeth-engaging element opposite the teeth-receiving portion, and wherein the base plate comprises oppositely disposed mounting flange members that are slidably received on the mounting portion of the foundation body;
a maxilla teeth-engaging element having a teeth-receiving portion, wherein the maxilla teeth-engaging element comprises a base plate mounted to a portion of the maxilla teeth-engaging element opposite the teeth-receiving portion of the maxilla teeth-engaging element, and wherein the base plate comprises oppositely disposed mounting flange members that are slidably received on the mounting portion of the foundation body; and
tongue-receiving member mounted to a forward portion of the maxilla teeth-engaging element and disposed centrally of the foundation body, wherein the tongue-receiving member provides a cavity for receiving a front part of a user's tongue in at least partially vacuum mode,
wherein the mandibular teeth-engaging element is slidably positioned on the mounting portion of the foundation body forward of the maxilla teeth-engaging element for relative positioning of a user's jaw, and
wherein the tongue depression portion urges against a surface portion of the user's tongue, close to the user's throat to substantially maintain unobstructed airways.

* * * * *